United States Patent [19]

Bader et al.

[11] Patent Number: 5,231,223

[45] Date of Patent: Jul. 27, 1993

[54] PROCESS FOR THE ARYLATION OF OLEFINS

[75] Inventors: Axel Bader, Leverkusen; Dieter Arlt, Cologne; Dietmar Fiedel, Odenthal-Voiswinkel; Stefan Meier, Leverkusen, all of Fed. Rep. of Germany

[73] Assignee: Bayer Aktiengesellschaft, Leverkusen, Fed. Rep. of Germany

[21] Appl. No.: 861,046

[22] Filed: Apr. 1, 1992

[30] Foreign Application Priority Data

Apr. 10, 1991 [DE] Fed. Rep. of Germany ....... 4111620
Apr. 10, 1991 [DE] Fed. Rep. of Germany ....... 4111653
Apr. 10, 1991 [DE] Fed. Rep. of Germany ....... 4111657

[51] Int. Cl.$^5$ .................... C07C 303/02; C07C 69/92
[52] U.S. Cl. .................... 562/87; 562/405; 566/8; 566/55
[58] Field of Search .................... 562/87, 405; 560/8, 560/55

[56] References Cited

U.S. PATENT DOCUMENTS 3,980,713  9/1976  Matsunaga et al. ............ 260/612 R

FOREIGN PATENT DOCUMENTS 0405389  1/1991  European Pat. Off. .

OTHER PUBLICATIONS

Kikukawa et al.; Tetrahedron (37), p. 31, 1981.
Bulletin of the Chemical Society of Japan, vol. 52, No. 9, Sep. 1979.
American Chemical Society. 1981, Palladium (O)-Catalyzed Arylation of Olefins by Arylamines and an Alkyl Nitrite, Kikukawa et al.
Arylation of Camphene with Arenediazonium Salts Catalyzed by Palladium Acetate, Synthesis, Nov. 1991, pp. 967-969, Wang Yong et al.

*Primary Examiner*—Marianne M. Cintins
*Assistant Examiner*—Michael B. Hydorn
*Attorney, Agent, or Firm*—Sprung Horn Kramer & Woods

[57] ABSTRACT

Substituted olefins of the formula (I)

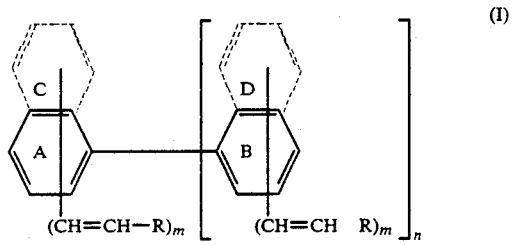

are prepared by reaction of a compound of the formula (II)

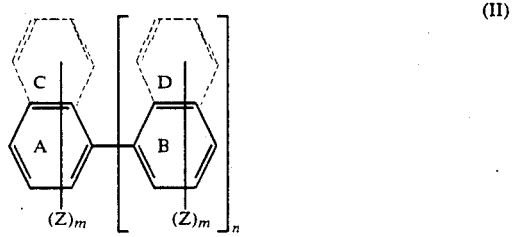

with a compound of the formula (III)

$$R-CH-CH_2$$

in the presence of an organic and/or inorganic palladium salt as a catalyst using water and/or an alcohol as a solvent, the substituents and indices being defined in the disclosure.

9 Claims, No Drawings

PROCESS FOR THE ARYLATION OF OLEFINS

The present invention relates to a process for the preparation of aryl olefins, characterised in that aryldiazonium salts are reacted with olefins in the presence of a palladium catalyst.

Preferably, the process according to the invention is used to prepare compounds of the formula (I)

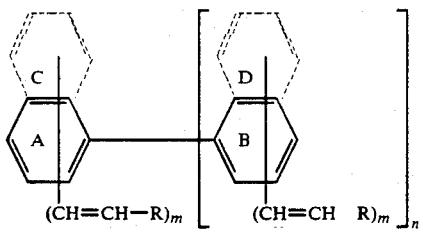

in which
R represents H, $C_1$–$C_{12}$-alkyl, optionally substituted $C_6$–$C_{10}$-aryl, optionally substituted hetaryl having 3 to 5 carbon atoms and 1 to 3 heteroatoms from the series comprising oxygen, sulphur and nitrogen, and also represents CN, COOM, COO-$C_1$–$C_{12}$-alkyl or $SO_3M$,
n represents 0 or 1,
where in the case in which n represents zero, the free valency on ring A is saturated by hydrogen,
m represents 1 or 2 and
the rings A, B, C, D and the aryl or hetaryl radicals mentioned can furthermore be substituted by one or more substituents from the series comprising fluorine, chlorine, bromine, iodine, $C_1$–$C_{12}$-alkyl, $C_1$–$C_{12}$-alkoxy, $CF_3$, $OCF_3$, CN, $NO_2$, COOM, COO-$C_1$–$C_{12}$-alkyl, $SO_3M$, CO-$C_1$–$C_{12}$-alkyl, CO-$C_6$–$C_{10}$-aryl, $C_6$–$C_{10}$-aryl, hetaryl, amino optionally substituted by $C_1$–$C_{12}$-alkyl, and
M denotes a customary cation
by reaction of a compound of the formula (II)

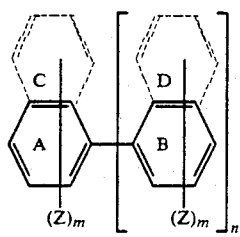

in which
Z represents $N_2 \oplus G$,
G represents a customary counter-ion and
m and n have the abovementioned meaning,
where in the case in which n represents zero, the free valency on ring A is saturated by hydrogen,
and the rings A, B, C and D can optionally be substituted by one or more of the substituents mentioned above for these rings,
with a compound of the formula (III)

 R—CH=CH$_2$     (III)

in which
R has the abovementioned meaning,
in the presence of a palladium catalyst.

In particular, the aryl radicals in the definition of R can represent the rings A and B or the fused ring systems AC or BD.

Customary counter-ions G are, for example, halide ions such as, for example, chloride or bromide, furthermore sulphate, hydrogen sulphate, nitrate, phosphate, acetate or tetrafluoroborate. Preferably, G represents a counter-ion from the series comprising chloride, sulphate, hydrogen sulphate, tetrafluoroborate and acetate.

If the rings A, B, C or D carry negatively charged substituents such as, for example, $SO_3^-$, then the compounds of the formula (II) can also be present as internal salts.

Suitable cations M are, for example, protons, alkali metal ions, in particular sodium and potassium ions, alkaline earth metal ions or ammonium ions.

Examples of compounds of the formula (II) which may be mentioned are: the isomeric diazobenzenesulphonic acids such as 2-, 3- or 4-diazobenzenesulphonic acid, the isomeric bis-(diazo)-benzenesulphonic acids such as 2,4-bis-(diazo)-benzenesulphonic acid or 2,5-bis-(diazo)-benzenesulphonic acid, the isomeric diazobenzenedisulphonic acids such as diazobenzene-2,4-disulphonic acid, diazobenzene-3,5-disulphonic acid and diazobenzene-2,5-disulphonic acid, the isomeric bis-(diazo)-benzenedisulphonic acids such as 1,4-bis-(diazo)-benzene-2,6-disulphonic acid or 1,3-bis-(diazo)-benzene-4,6-disulphonicacid, furthermore 2-, 3- or 4-diazobenzoic acid, 2-, 3- or 4-diazobenzoic acid $C_1$–$C_{12}$-alkyl esters, such as methyl 2-, 3- or 4-diazobenzoate, ethyl 2-, 3- or 4-diazobenzoate, n-propyl 2-, 3- or 4-diazobenzoate, i-propyl 2-, 3- or 4-diazobenzoate, n-butyl 2-, 3- or 4-diazobenzoate, 2-, 3- or 4-diazobenzoic acid $C_6$–$C_{10}$-aryl esters such as phenyl 2-, 3- or 4-diazobenzoates, 3- or 4-diazobenzene-1,2-dicarboxylic acid, 3- or 4-diazobenzene-1,2-dicarboxylic acid di-$C_1$–$C_{12}$-alkyl esters such as dimethyl 3- or 4-diazobenzene-1,2-dicarboxylate or diethyl 3- or 4-diazobenzene-1,2-dicarboxylate, 3- or 4-diazobenzene-1,2-dicarboxylic anhydride, 2-, 3- or 4-diazobenzonitrile, 3- or 4-diazophthalonitrile or diazo-$C_1$–$C_{12}$-alkoxybenzenes such as 2-, 3- or 4-diazomethoxybenzene, 2-, 3- or 4-diazoethoxybenzene, 2-, 3- or 4-diazo-tert-butoxybenzene, 2-, 3- or 4- diazophenyl-$C_6$–$C_{10}$-aryl ethers, 2-, 3- or 4-diazonitrobenzene, 2-, 3- or 4-diazofluorobenzene, 2-, 3- or 4-diazochlorobenzene, 2-, 3- or 4-diazobromobenzene, 2-, 3- or 4-diazoiodobenzene, the isomeric diazofluorochlorobenzenes such as 3-diazo-2-fluorochlorobenzene, the isomeric diazobromochlorobenzenes, the isomeric diazofluorobromobenzenes, the isomeric diazodifluorobenzenes, the isomeric diazodichlorobenzenes, the isomeric diazodibromobenzenes, the isomeric diazodiiodobenzenes, 2-, 3- or 4-diazo(trifluoromethylbenzene), (2-, 3- or 4-diazophenyl)-$C_1$–$C_{12}$-alkyl ketones such as 2-, 3- or 4-diazoacetophenone, (2-, 3- or 4-diazophenyl)-$C_6$–$C_{10}$-aryl ketones such as 2-, 3- or 4-diazobenzophenone, 2-, 3- or 4-diazo-$C_1$–$C_{12}$-alkylbenzenes such as 2-, 3- or 4-diazotoluene, the isomeric 2-, 3- or 4-diazodi-$C_1$–$C_{12}$-alkylbenzenes such as 3- or 4-diazo-o-xylene, the isomeric bis-(diazo)-$C_1$–$C_{12}$-alkylbenzenes, such as 2,3-bis-(diazo)-toluene, 2,4-bis-(diazo)-toluene, 2,5-bis-(diazo)-toluene or 2,6-bis-(diazo)-toluene, also bis-(diazo)-di-$C_1$–$C_{12}$-alkylbenzenes, 2-, 3- or 4-diazo-$C_6$–$C_{10}$-aryl-benzenes such as 2-, 3- or 4-diazobiphenyl, 2-, 3- or 4-diazoaminobenzene, or 2-, 3- or 4-diazophenol. Others which may additionally be mentioned are the isomeric diazonaphthalenesulphonic acids such as 8-diazo-2-naphthalenesulphonic acid, 8-diazo-1-naphthalenesulphonic acid, 7-diazo-1-naphthalenesulphonic acid, 6-diazo-2-naphthalenesulphonicacid,5-diazo-2-naphthalenesulphonic acid, 5-diazo-1-naphthalenesulphonic acid, 4-diazo-2-naphthalenesulphonicacid,2-diazonaphthalene-1-sulphonic acid, 1-diazo-2-naphthalenesulphonic acid, the isomeric diazonaphthalenedisulphonic acids such as 7-diazo-1,3-naphthalenedisulphonic acid, 3-diazo-2,6-naphthalenedisulphonic acid, 3-diazo-2,7-naphthalenedisulphonic acid, 4-diazo-1,3-naphthalenedisulphonic acid, 4-diazo-1,5-naphthalenedisulphonic acid, 4-diazo-1,6-naphthalenedisulphonic acid, 4-diazo-1,7-naphthalenedisulphonic acid, 4-diazo-2,6-naphthalenedisulphonic acid, 6-diazo-1,3-naphthalenedisulphonic acid, 8-diazo-1,3-naphthalenedisulphonic acid, 3-diazo-1,5-napthalenedisulphonic acid, 4-diazo-2,7-naphthalenedisulphonic acid, 5-diazo-1,3-napthalenedisulphonic acid, the isomeric bis-(diazo)-naphthalenesulphonic acids and bis-(diazo)-naphthalenedisulphonic acids such as 3,4-bis-(diazo)-1-naphthalenesulphonic acid, 4,5-bis-(diazo)-1-naphthalenesulphonic acid, 3,8-bis-(diazo)-1,5-naphthalenedisulphonic acid, 4,8-bis-(diazo)-2,6-naphthalene-disulphonic acid, 5,6-bis-(diazo)-1,3-naphthalenedisulphonic acid, 4,5-bis-(diazo)-2,7-naphthalenedisulphonic acid, and also bis-(diazo)-biphenyl-mono- and disulphonic acids such as 4,4'-bis-(diazo)-biphenyl-3-sulphonic acid and 4,4'-bis-(diazo)-3,3'-disulphonic acid.

Examples of compounds of the formula (III) which may be mentioned are ethylene, propylene, butylene, optionally substituted vinyl-$C_6$-$C_{10}$-aromatics such as styrene or the isomeric vinylnaphthalenes, 2-, 3- or 4-fluorostyrene, 2-, 3- or 4-chlorostyrene, 2-, 3- or 4-bromostyrene, 2-, 3- or 4-iodostyrene, 2-, 3- or 4-cyanostyrene, 2-, 3- or 4-nitrostyrene, 2-, 3- or 4-styrenecarboxylic acid, 2-, 3- or 4-styrenecarboxylic acid $C_1$-$C_{12}$-alkyl esters such as methyl 2-, 3- or 4-styrenecarboxylate, 2-, 3- or 4styrenecarboxylic acid $C_6$-$C_{12}$-aryl esters such as phenyl 2-, 3- or 4-styrenecarboxylate, 2-, 3- or 4-styrenesulphonic acid or its salts, 3- or 4-vinylphthalic acid, 3- or 4-vinylphthalic acid $C_1$-$C_{12}$-alkyl esters such as dimethyl 3- or 4-vinylphthalate, 3- or 4-vinylphthalic acid di-$C_6$-$C_{10}$-aryl esters such as diphenyl 3- or 4-vinylphthalate, 3- or 4-vinylphthalic anhydride, vinylhetaryls such as N-vinylimidazole or 2- or 4-vinylpyridine, and also acrylonitrile, acrylic acid, acrylic acid $C_1$-$C_{12}$-alkyl esters such as methyl acrylate, ethyl acryate, N-propyl acrylate and 2-ethyl-hexyl acrylate, vinylsulphonic acid or its salts.

The process according to the invention is carried out in the presence of a palladium catalyst.

Palladium catalysts which can be used are metallic palladium, organic or inorganic palladium compounds. Palladium can be employed as palladium black or as palladium on supports, such as, for example, palladium on carbon. Suitable organic or inorganic palladium compounds are preferably palladium salts such as, for example, the chloride, the bromide, the iodide, the nitrate, the sulphate, the acetate or the propionate; the said halides and the acetate are preferred.

The said substances can be employed as catalysts on their own or in any suitable mixtures.

In certain cases, it can be of advantage in carrying out the process according to the invention to add compounds which form complexes with palladium or palladium salts. Suitable complexing agents are, for example, arylnitriles optionally substituted by sulpho groups, such as benzonitrile, or $C_1$-$C_4$-alkylnitriles such as acetonitrile or phosphites such as, for example, triphenyl phosphite. Preferred complexing agents are phosphanes such as triarylphosphanes of the formula (IV)

in which
Ar represents optionally substituted $C_6$-$C_{10}$-aryl, preferably phenyl optionally substituted by methyl,
a, b and c, independently of one another, represent 0, 1 or 2, where the sum of a, b and c is preferably at most 3, and
M has the abovementioned meaning,
and bis(diarylphosphane)-alkanes of the formula (V)

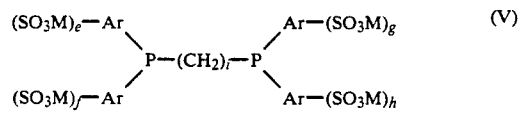

in which
i represents 1, 2, 3 or 4,
Ar represents optionally substituted $C_6$-$C_{10}$-aryl, preferably phenyl optionally substituted by methyl,
e, f, g and h, independently of one another, represent 0 or 1, where the sum of e, f, g and h is preferably at most 4, and
M has the abovementioned meaning.

Examples of triarylphosphanes of the formula (IV) are tri-o-tolylphosphane, triphenylphosphane, triphenylphosphane tri-(sodium sulphonate), triphenylphosphane di-(sodium sulphonate) and triphenylphosphane mono-(sodium sulphonate).

Examples of bis(diarylphosphane)-alkanes of the formula (V) are bis(diphenylphosphane)-methane, -ethane, -propane or -butane, bis-(diphenylphosphane)methane mono-, di-, tri- or tetra-(sodium sulphonate), bis-(diphenylphosphane)-ethane mono-, di-, tri- or tetra-(sodium sulphonate) and bis-(diphenylphosphane)propane mono-, di-, trior tetra-(sodium sulphonate).

Also suitable as complexing agents are trihetarylphosphanes, optionally substituted by sulpho groups, such as, for example, trifurylphosphane. Dibenzylideneacetone optionally substituted by sulpho groups is furthermore suitable.

If the process according to the invention is carried out using water as the solvent, the complexing agents in general preferred are those which contain hydrophilic radicals such as, for example, COOM, OH, $NH_2$ or $SO_3M$, where M has the abovementioned meaning, in particular those of the formula (IV) which contain 1 to 3 sulpho groups, and/or those of the formula (V) which contain 1 to 4 sulpho groups.

If the process according to the invention is carried out in an organic solvent, sulpho group-free complexing agents are in general preferred, in particular those of the formula (IV) in which the sum of a, b and c is zero and/or of the formula (V) in which the sum of e, f, g and h is zero.

The complexes are preferably produced in situ; however, preformed complexes of the said complexing agents with palladium can also be employed. Examples of such preformed complexes are tetrakis(triphenylphosphane)palladium, bis(dibenzylideneacetone)palladium, tris-(dibenzylideneacetone)-dipalladium, bis(triphenylphosphane)palladium dichloride, bis(benzonitrile)palladium dichloride or alternatively bis(acetonitrile)palladium dichloride.

Mixtures of the said complexing agents can also be employed. The said complexing agents can be employed in excess; in general 2 to 40 mol of the said complexing agents are used per mole of palladium. The catalysts are in general used in an amount of 0.001 to 5 mol%, preferably from 0.005 to 1 mol%, relative to the compound of the formula (II).

It may be of advantage to carry out the process according to the invention in the presence of bases. Suitable bases are, for example, open-chain or cyclic secondary or tertiary amines, such as, for example, diethylamine, triethylamine, pyrrolidine, piperidine, piperazine, diazabicyclooctane (DABCO), diazabicyclononene (DBN), diazabicycloundecene (DBU), arylamines, aryldiamines, alkali metal and alkaline earth metal salts of aliphatic and aromatic carboxylic acids, such as, for example, sodium acetate, potassium acetate or calcium acetate, sodium propionate or potassium propionate, sodium laurate or potassium laurate, sodium benzoate or potassium benzoate, alkali metal and alkaline earth metal carbonates, such as, for example, potassium carbonate, sodium carbonate, lithium carbonate, calcium carbonate, alkali metal or alkaline earth metal hydrogen carbonates, such as, for example, sodium hydrogen carbonate, calcium hydrogen carbonate or alternatively alkali metal or alkaline earth metal hydroxides, such as, for example, lithium hydroxide, potassium hydroxide, sodium hydroxide, calcium hydroxide and barium hydroxide. The said bases can be employed on their own or in any desired mixtures with one another.

The process according to the invention is preferably carried out in an inorganic or organic solvent. Suitable solvents are, for example, water, amides such as dimethylformamide or N-methylpyrrolidone, sulphoxides such as dimethyl sulphoxide, ketones such as acetone, ethers such as di-$C_2$-$C_8$-alkyl ethers or alternatively tetrahydrofuran or dioxane or ethylene glycol monomethyl ether or ethylene glycol dimethyl ether or propylene glycol monomethyl ether, straight-chain or branched primary, secondary or tertiary $C_1$-$C_{12}$-alcohols or diols such as methanol, ethanol, ethylene glycol, propanol, isopropanol, n-butanol, tert-butanol, tert-amyl alcohol, 2-ethylhexanol, aromatic or aliphatic nitriles such as benzonitrile or acetonitrile, optionally halogenated aromatic or aliphatic hydrocarbons such as toluene, chlorobenzene, dichlorobenzene, chloroform, methylene chloride and carbon tetrachloride.

Mixtures of the abovementioned solvents can also be employed, even those which form two-phase systems.

The process according to the invention is in general carried out at temperatures between −20° and 150° C., preferably between 0° and 120° C., particularly preferably between 20° and 90° C.

In particular, the process according to the invention is used to prepare compounds of the formula (Ia)

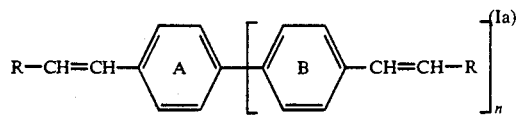

in which

R and n have the meaning indicated for formula (I), where, in the case in which n represents zero, the free valency on the ring A is saturated by hydrogen or a substituent mentioned for the ring A, and the rings A and B can carry further substituents, as indicated in formula (I) for these rings, by reaction of a compound of the formula (IIa)

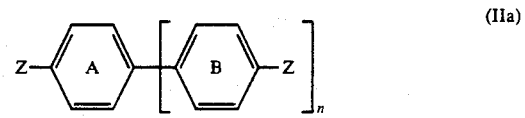

in which

Z and n have the meaning indicated for formula (II), and the rings A and B can carry further substituents, as indicated in formula (II) for these rings, with a compound of the formula (III).

In an embodiment of the process according to the invention which is also preferred, compounds of the formula (II), preferably of the formula (IIb)

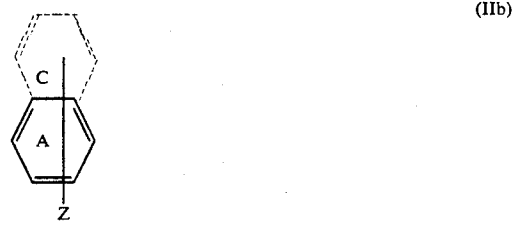

in which

Z has the meaning indicated for formula (II) and the rings A and C optionally carry further radicals, as defined in formula (I) for these rings, are reacted with ethylene (IIIa).

In this manner, preferably compounds of the formulae

and

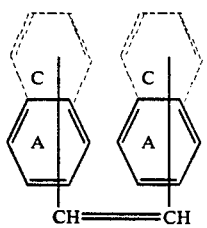

(Ic)

in which the rings A and C can each carry further substituents, as indicated under formula (I) for these rings, are prepared.

In this case, the ratio of vinylaromatics (Ib) to diarylethylene compounds (Ic) can be influenced by the choice of the reaction conditions, in particular also by the manner of ethylene introduction.

In general, vinylaromatics (Ib) are preferably obtained if the reaction is carried out under an ethylene pressure of 6 to 100 bar, preferably of 8 to 50 bar. It is disadvantageous that it is necessary in this case to work in autoclaves.

This reaction, however, can also be carried out at lower pressures than the abovementioned pressures if the ethylene is passed into the reaction mixture with the aid of an intensive aeration device.

Preferably, the reaction with ethylene is carried out at normal pressure or slightly elevated pressure, the ethylene being passed into the reaction mixture with the aid of an intensive aeration device.

Suitable intensive aeration devices are, for example: surface aerators or volume aerators such as rotary aerators, cylinder aerators, water jet aerators, immersed jet aerators, pipe injector stirrers, stirrers having a separate gas supply, immersed aerators, frits, perforated plates, static mixers or a two-substance nozzle through which the reaction mixture and the ethylene are simultaneously passed.

It may be favourable to supplement the intensive aeration device by an additional mixing element to homogenise the reaction mixture.

Such intensive aeration devices and mixing elements are known to the person skilled in the art, for example from Ullmann's Encyclopedia of Industrial Chemistry, 5th edition, vol. B2, VCH Verlagsgesellschaft, Weinheim (1988).

The process products of the formula (I) are known in some cases.

In particular, the process according to the invention is used to prepare compounds of the formula (VI)

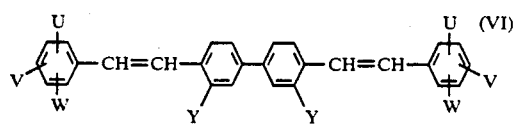

in which
Y represents H or SO$_3$M,
U, V and W, independently of one another, represent H, F, Cl, methyl, methoxy, CF$_3$, CN, OCF$_3$, SO$_3$M, COOM or COO-C$_1$-C$_{12}$-alkyl,
and M has the abovementioned meaning,
of the formula (VII)

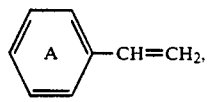

(VII)

in which
the ring A can carry one or more of the substituents mentioned above under formula (I) for this ring,
and of the formulae (VIII) and (VIIIa)

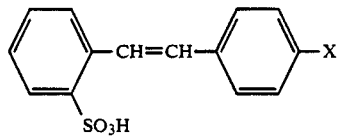

(VIII)

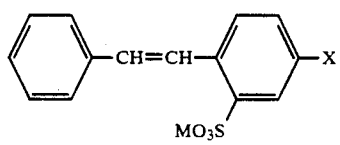

(VIIIa)

in which
X denotes chlorine, bromine or iodine and
M has the abovementioned meaning.

The compounds of the formulae (VI), (VII), (VIII) and (VIIIa) are, in some cases, known optical brighteners or precursors for optical brighteners.

Hitherto, a process was preferably used in which, instead of compounds of the formula (II), the corresponding halogen compounds such as, for example, bromobenzene-2-sulphonic acid were employed (DE-A 2,325,302). Halogenobenzenesulphonic acids free from positional isomers, like the said bromobenzene-2-sulphonic acid, however, are as a rule less easily accessible than the compounds of the formula (II), and they are even preferably prepared from compounds of the formula (II) by the Sandmeyer reaction. The process according to the invention allows the halogenobenzenesulphonic acid step to be eliminated.

Other preferred process products correspond to the formula (IX)

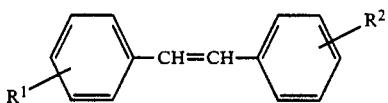

(IX)

in which
R$^1$ and R$^2$, independently of one another, represent H, COOM, COO-C$_1$-C$_{12}$-alkyl, NO$_2$, COO-C$_6$-C$_{10}$-aryl, CO-C$_1$-C$_{12}$-alkyl, CO-C$_6$-C$_{10}$-aryl, O-C$_6$-C$_{12}$-aryl or O-C$_1$-C$_{12}$-alkyl,
or to the formula (X)

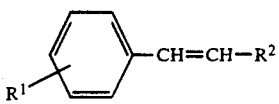

(X)

in which
R$^1$ and R$^2$ have the abovementioned meaning.
Examples of compounds of the formula (IX) which may be mentioned are: stilbene-2-carboxylic acid, stilbene-3- carboxylic acid, stilbene-4-carboxylic acid and the straight-chain or branched $C_1-C_{12}$-alkyl esters of these carboxylic acids which are deriived, for example, from the following alcohols: methanol, ethanol, n-propanol, i-propanol, n-butanol, i-butanol, tert-butanol, and the isomeric pentanols and hexanols.

The following may also be mentioned: stilbene-4,4'-dicarboxylic acid, stilbene-3,3'-dicarboxylic acid, stilbene-2,2'-dicarboxylic acid and the straight-chain or branched $C_1-C_{12}$-alkyl esters of these carboxylic acids which are also derived from the abovementioned alcohols.

Stilbene-2-carboxylic acid and stilbene-2-carboxylic acid alkyl esters are precursors, which are important and simply and economically accessible by the process according to the invention, for dibenzosuberone, an intermediate for pharmaceuticals.

Examples of compounds of the formula (X) which may be mentioned are in particular compounds in which $R_1$ represents H or $C_1-C_{12}$-alkoxy and $R^2$ represents COOH or $COO-C_1-C_{12}$-alkyl, such as, for example, cinnamic acid or substituted cinnamic acid esters. Mention may be made of 2-ethyl-hexyl p-methoxycinnamate (XI), an important UV absorber Stuttgart 1965, volume X/3, page 39 et seq. for single or double diazotisation of aromatic diamines.

The diazonium salts of the formula (II) or (IIa) and (IIb) can be isolated in certain cases and employed in the process according to the invention. However, it is also possible to employ the solution or the suspension of the diazonium salt produced in the preparation. The reaction can be performed in this solution or suspension of the diazonium salt by treating with the compound of the formula (III), if appropriate a base and if appropriate a complexing agent, and adding palladium catalyst and heating the reaction mixture, if necessary, until gas is evolved.

However, the process according to the invention can also be carried out by first introducing, in a suitable solvent, palladium catalyst, if appropriate a complexing agent and if appropriate a base, and the compound of the formula (III), and then metering in the diazonium salt of the formula (II) or (IIa) or (IIb) or the solution or suspension of the corresponding diazonium salt at the temperature necessary for reaction, for example from an optionally cooled storage vessel.

Particularly if the compound of the formula (III) is liquid at the reaction temperature, a solvent can be

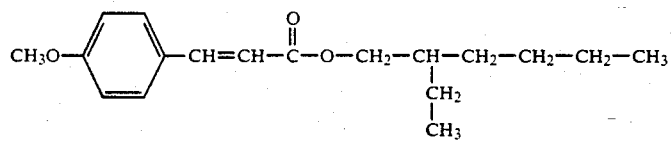
(XI)

The compounds of the formula (II) can be prepared in a manner known per se from compounds of the formula (XII)

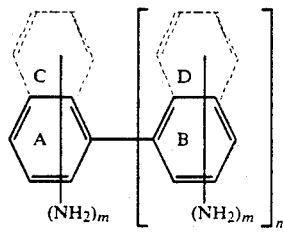
(XII)

in which
m and n have the abovementioned meaning,
and the rings A, B, C and D optionally carry further substituents as mentioned under formula (I) for these rings,
for example by treating with nitrite ions or with alkyl nitrites in the presence of acids in aqueous or organic solution (compare, for example, Houben-Weyl, Methoden der Organischen Chemie (Methods of organic chemistry), volume X/3, Georg Thieme Verlag, Stuttgart 1965, page 7 et seq.).

During diazotisation in organic solution, it may be advantageous to remove the water formed, for example by means of water-binding additives. Such water-binding additives are, for example, sodium sulphate, magnesium sulphate, copper sulphate, calcium chloride or alternatively molecular sieves.

In certain cases, it is possible to perform specific diazotisations in the compounds of the formula (XII) in the presence of several $NH_2$ groups, see, for example, Houben-Weyl, Methoden der organischen Chemie (Methods of organic chemistry), Georg Thieme Verlag, dispensed with in this process variant.

The Pd catalyst can be recovered after reaction is complete, the manner of recovery depending, inter alia, on the nature of the catalyst employed and of the solvent used. In principle, a partition of reaction product and catalyst in different phases, which can be readily the reaction product is soluble in the reaction medium, but the catalyst is not, whether it is on a support such as, for example, active carbon or because it is present as metallic palladium, then the catalyst can be separated off by simple filtration and the reaction product can be isolated from the filtrate. Conversely, if a soluble catalyst is present in the reaction mixture, for example a Pd complex, in addition to undissolved product, the product can first be isolated by filtration and the catalyst can then be isolated from the filtrate. If appropriate, the filtrate containing the catalyst can also be fed back into the process according to the invention again. If both the catalyst and the reaction product are present in dissolved form, the separation can be carried out by means of suitable measures such as, for example, salting-out of the product, precipitation of one component by addition of a solvent of suitable polarity or extraction of one component using a suitable solvent. If catalyst and reaction product are insoluble in the reaction medium, both can be jointly isolated by filtration and then separated, for example by treating with a solvent which only dissolves one component.

The catalyst can, if appropriate after suitable working-up, be fed back into the process again.

EXAMPLES

Example 1

13 ml of conc. HCl were added to a solution of 5.2 g of aniline-2-sulphonic acid and 1.3 g of NaOH in 40 ml of H₂O and 2.3 g of NaNO₂ dissolved in 5 ml of water were added dropwise at 0° to 5° C. After about 10 min, the mixture was neutralised with dilute NaOH. 3.46 g of Na₂CO₃ were added, ethylene was passed in via a pipe injector stirrer, 0.068 g of Pd(OAc)₂ was added and the mixture was stirred at room temperature for 2 h. It was then evaporated to dryness and the product was extracted from the solid residue with methanol After evaporation of the methanol, 5.3 g (86%) of styrene-2-sulphonic acid, Na salt remained.

¹H-NMR (DMSO-d:): 5.2 (dd, 1H), 5.7 (dd, 1H), 7.15-7.4 (m,<2H), 7.55-7.85 (m, 3H).

Example 2

First 18 g of glacial acetic acid and then 11.7 g of isoamyl nitrite were added dropwise to 17.3 g of aniline-2-sulphonic acid in 300 ml of methanol and the mixture was stirred for half an hour at room temperature. Ethylene was passed in via a pipe injector stirrer, and first 113 mg of Pd(OAc)₂ and then, in portions, 27.6 g of potassium carbonate were added. After addition was complete, the mixture was stirred for a further 1 hour, then some of the methanol was distilled off. Undissolved salts were filtered off and the filtrate was evaporated to dryness.

Yield: 18.4 g (83%) of styrene-2-sulphonic acid, K salt.

Example 3

The procedure was as in Example 2, but instead of potassium carbonate sodium carbonate was used.

Yield: 16.3 g (79%) of styrene-2-sulphonic acid, Na salt.

Example 4

The procedure was as in Example 2, but instead of potassium carbonate a solution of 16 g of NaOH in 200 ml of methanol was slowly added.

Yield: 17.9 g (87%) of styrene-2-sulphonic acid, Na salt.

Example 5

The procedure was as in Example 4, but instead of Pd(OAc)₂ palladium black was used.

Yield: 16.7 g (81%) of styrene-2-sulphonic acid, Na salt.

Example 6

The procedure was as in Example 4, but instead of Pd black 10% Pd on carbon was used.

Yield: 15.2 g (74%) of styrene-2-sulphonic acid, Na salt.

Example 7

5.32 ml of isoamyl nitrite were added dropwise between 10 and 20° C. to 6.88 g of 4,4'-diaminobiphenyl-3,3'-disulphonic acid and 6.9 ml of glacial acetic acid in 100 ml of methanol. 5.2 g of styrene and 45 mg of Pd(OAc)₂ were then added and a solution of 6.4 g of NaOH in 100 ml of methanol was added dropwise. The mixture was stirred at room temperature for 2 hours and concentrated to dryness, the residue was taken up in water, the solution was filtered and the product was salted out.

Yield: 8.7 g (79%) of 4,4'-distyrylbiphenyl-3,3'-disulphonic acid, di-Na salt.

¹H-NMR spectrum:=7.21 (d, 2H), 7.30 (m, 2H), 7.41 (m, 4H), 7.57 (m, 4H), 7.68 (m, 2H), 7.92 (m, 2H), 8.18 (d, 2H), 8.33 (d, 2H).

Example 8

A solution of 2.3 g of NaNO₂ in 5 ml of water was added dropwise at 0° to 5° C. to 5.7 g of 2-aminobenzenesulphonic acid and 13 ml of conc. HCl in 40 ml of water. The precipitate was filtered off with suction and suspended in 100 ml of acetonitrile together with 4.06 g of sodium acetate. Under a pressure of 50 bar of ethylene, a solution of 347 mg of tetrakis-(triphenylphosphine)palladium in 20 ml of toluene was added. After 2 hours at room temperature, the precipitate was filtered off with suction and dried. 4.4 g (71%) of styrene-2-sulphonic acid, Na salt, were obtained, which, according to the ¹H-NMR sepctrum, was only slightly contaminated with sodium acetate.

¹H-NMR spectrum=5.2 (dd, 1H), 5.7 (dd, 1H), 7.15 to 7.40 (m, 2H), 7.5 to 7.9 (m, 3H)

Example 9

The diazonium salt of 2-aminobenzenesulphonic acid was prepared as described in Example 8, filtered off with suction and initially introduced into 100 ml of water together with 3.45 g of sodium carbonate. Under a pressure of 50 bar of ethylene, a solution of 68 mg of Pd(OAc)₂ and 560 mg of a compound of the formula

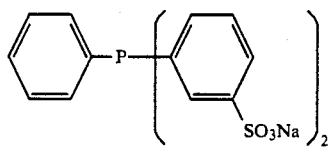

in 10 ml of water was added at room temperature and the reaction mixture was stirred at room temperature for 2 hours. It was then concentrated to dryness and the product was extracted from the residue with methanol. 4.8 g (78%) of styrene-2-sulphonic acid, Na salt, were obtained.

Example 10

The diazoni-m salt of 2-aminobenzenesulphonic acid was prepared as in Example 9, and the resulting suspension was neutralised with aqueous sodium hydroxide solution and then treated with 3.46 g of sodium carbonate. Under a pressure of 50 bar of ethylene, a solution of 68 mg of Pd(OAc)₂ and 560 mg of a compound of the formula

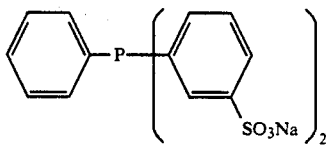

in 10 ml of water was added at room temperature and the reaction mixture was stirred at room temperature for 2 hours. After working up as described in Example 9, 4.4 g (71%) of styrene-2-sulphonic acid, Na salt, were obtained.

Example 11

The procedure was as in Example 10, but instead of the compound of the formula

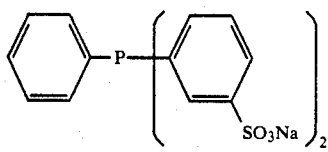

430 mg of the compound of the formula

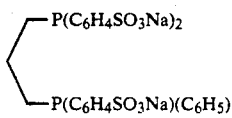

were added. Yield: 4.7 g (77%) of styrene-2-sulphonic acid, Na salt.

Example 12

10.1 g of aniline-2-sulphonic acid (85%) were dissolved in 40 ml of sodium hydroxide solution (6%) and treated with 40 ml of conc. HCl. 12 ml of aqueous NaNO$_2$ solution were added dropwise to the resulting suspension at a temperature of 0° to 5° C. and the mixture was stirred at this temperature for 30 minutes. 50 g of sodium acetate, 300 ml of methanol and 0.5 g of bis(dibenzylideneacetone-2,2'-disulphonic acid disodium salt)palladium(0) were added successively and the mixture was stirred for 3 hours at 20° C. under an ethylene pressure of 20 bar. It was then filtered and evaporated to dryness, and the residue was stirred with ethanol. The mixture was again filtered and evaporated. 7.4 g (72%) of styrene-2-sulphonic acid, Na salt, were obtained.

The bis(dibenzylideneacetone-2,2'-disulphonic acid disodium salt)palladium(0) used was obtained as follows:

4.4 g of dibenzylidene-2,2'-disulphonic acid disodium salt and 3.0 g of sodium acetate were dissolved in 150 ml of methanol and heated to 60° C. under a nitrogen atmosphere. After addition of 0.71 g of palladium(II) chloride, the mixture was stirred for a further 4 hours at this temperature and then cooled, and the solid was filtered off with suction. The filter residue was dried in vacuo and 2.8 g (71%) of bis(dibenzylideneacetone-2,2'-disulphonic acid disodium salt)palladium(0) were obtained.

The dibenzylideneacetone-2,2'-disulphonic acid disodium salt used as the starting material was prepared in the following way: A solution of 44 g of benzaldehyde-2-sulphonic acid, Na salt, and 5.8 g of acetone in 100 ml of water was added at 25° C., in the course of 15 minutes to a solution of 30 g of NaOH in 150 ml of water. The mixture was stirred for a further 30 minutes at 25° C., then filtered and the filter residue was washed with a little ice-water. After drying the filter cake in vacuo, 37.5 g (85%) of dibenzylideneacetone-2,2'-disulphonic acid disodium salt remained.

Example 13

10 g of HCl gas were passed into a suspension of 17.3 g of aniline-2-sulphonic acid in 300 ml of methanol at 40° C. The mixture was stirred at this temperature for 2 hours, then cooled to 20° C. and treated dropwise with 12.6 g of amyl nitrite. After a further hour, 34 g of sodium acetate were added and 20 g of ethylene were passed into the suspension via an aerating stirrer. 0.7 g of bis(benzonitrile)palladium(II) chloride was then added and the mixture was stirred for 5 hours under a brisk stream of ethylene. After this time, the solid was filtered off with suction and the filtrate was evaporated to dryness. 15.8 g (77%) of styrene-2-sulphonic acid, Na salt, remained.

Example 14

Example 13 was repeated, but instead of aniline-2-sulphonic acid the same amount of aniline-4-sulphonic acid and instead of methanol the same volume of isopropanol were used. 15.0 g (73%) of styrene-4-sulphonic acid, Na salt, were obtained.

Example 15

13.0 g of aniline-2-sulphonic acid were suspended in 200 ml of methanol and treated with 20 g of glacial acetic acid. Under a nitrogen atmosphere, 9.5 g of amyl nitrite were added dropwise at a temperature of 0° to 5° C. and the suspension was stirred for 1 hour. A solution of 15 g of NaOH in 100 ml of methanol was then added dropwise at such a rate that the temperature of the mixture did not exceed 20° C. After addition of 0.5 g of bis(dibenzylideneacetone)palladium(0), the mixture was stirred at 20° C. for 3 hours under an ethylene pressure of 20 bar, the solid was then filtered off with suction and the filtrate was evaporated to dryness. 12.1 g (78%) of styrene-2-sulphonic acid, Na salt, were obtained.

Example 16

If instead of aniline-2-sulphonic acid the same amount of aniline-3-sulphonic acid was used, 11.0 g (71%) of styrene-3-sulphonic acid, Na salt, were obtained by the method indicated in Example 15.

Example 17

20.7 g of sodium nitrite in 50 ml of water are added dropwise at 0°-5° C. to 41.1 g of anthranilic acid and 24 ml of conc. H$_2$SO$_4$ in 300 ml of water and the mixture is stirred at this temperature for 20 minutes. An excess of nitrite which may be present is destroyed by addition of sulphamic acid. The solution of the diazonium salt prepared in this way is added dropwise at about 60° C. to a rapidly stirred mixture of 62.4 g of styrene and 20 ml of water, and immediately after the start of addition the mixture is treated with 68 mg of Pd(OAc)$_2$. After addition and evolution of gas are complete, the mixture is allowed to cool and the solid is filtered off with suction, washed with warm water and dried at 60° C. 62.5 g (93%) of stilbene-2-carboxylic acid of m.p. 158°-159° C. are obtained, Lit 158-160° C., Chem. Ber. 27, 2506 (1894).

$^1$H-NMR (CDCl$_3$):δ=7.0 (d, 1H) 7.2-7.4 (m, 4H) 7.43-7.60 (m,3H), 7.7 (m, 1H); 7.95-8.15 (m, 2H), 10.2 (broad, 1H).

Example 18

A solution of 13.8 g of sodium nitrite in 30 ml of water is added dropwise at 0°-5° C. to 30.2 g of methyl anthranilate and 16 ml of conc. H$_2$SO$_4$ in 200 ml of water and after addition is complete the mixture is stirred for a further 15 minutes at this temperature. An excess of nitrile which may be present is destroyed by addition of sulphamic acid. The mixture is then treated with 16.4 g of sodium acetate, 41.6 g of styrene and 45 mg of Pd(OAc)$_2$ and heated to 60°-70° C. until evolution of gas has ended. After evolution of gas is complete, the phases are separated, the aqueous phase is additionally extracted once by shaking with methylene chloride, and the combined organic phases are washed twice with water, dried and freed of solvent. 45.6 g (95%) of methyl stilbene-2-carboxylate are obtained, 90% pure according to GC (SE 30, 100°-300° C.).

$^1$H-NMR (CDCl$_3$):δ=3.9 (s, 3H), 6.98 (d, 1H), 7.2-7.6 (m, 7H), 7.7 (m, 1H), 7.85-8.05 (m, 2H).

Example 19

The procedure is as in Example 18, but only 22.5 mg of Pd(OAc)$_2$ are employed. 44.3 (93%) of methyl stilbene-2-carboxylate are obtained, 84% pure according to GC (SE 30, 100°-300° C.).

Example 20

117 g of amyl nitrite are added slowly to a solution, cooled to about 10° C., of 123 g of p-anisidine and 100 ml of conc. H$_2$SO$_4$ in 400 ml of methanol and the mixture is stirred without cooling for a further 40 minutes after addition is complete It is treated with 95 g of methyl acrylate and 112 mg of Pd(OAc)$_2$ and heated to about 55° C. until evolution of gas has ended. After cooling, the solid is filtered off with suction, washed with water and dried at 40° C. 167 g (87%) of methyl p-methoxycinnamate are obtained, m.p. 88°-89° C., Lit 89° C.

Example 21

The procedure is as in Example 20, but amyl nitrite is replaced by the corresponding amount of methyl nitrite. Yield 180 g (94%).

Example 22

117 g of amyl nitrite are added slowly to a mixture, cooled to about 10° C., of 123 g of p-anisidine and 100 ml of conc. H$_2$SO$_4$ in 500 ml of 2-ethylhexanol and the mixture is stirred for a further 40 min after addition is complete. It is treated with 202 g of 2-ethylhexyl acrylate and 112 mg of Pd(OAc)$_2$ and heated to about 65° C. until evolution of gas has ended.

The mixture is diluted with water and the product is extracted with methylene chloride. The organic phase is additionally washed twice with water, dried and evaporated. The residue is distilled in vacuo. 241 g (83%) of 2-ethylhexyl p-methoxycinnamate are obtained.

$^1$H-NMR (CDCl$_3$):δ=0.8-1.9 (m, 15H), 3.8 (s, 3H), 4.1 (m, 2H), 6.3 (d, 1H), 6.9 (m, 2H), 7.5 (m, 2H), 7.7 (d, 1H).

What is claimed is:

1. A process for preparing a substituted olefin of the formula (I)

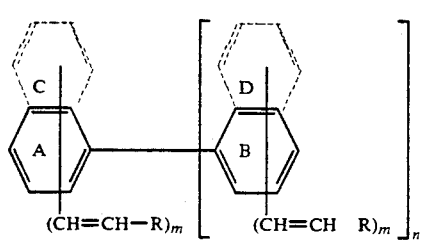

in which
R represents CN, COOM, COO-C$_1$-C$_{12}$-alkyl, SO$_3$M, H—, C$_1$-C$_{12}$-alkyl, optionally substituted C$_6$-C$_{10}$-aryl or optionally substituted hetaryl having 3 to 5 carbon atoms and 1 to 3 heteroatoms selected from the group consisting of oxygen, sulphur and nitrogen,
n represents 0 to 1,
where in the case in which n represents zero, the free valency on ring A is saturated by hydrogen,
m represents 1 or 2,
the rings A, B, C, D and the aryl or hetaryl radicals of R are optionally substituted by at least one substituent selected from the group consisting of fluorine, chlorine, bromine, iodine, C$_1$-C$_{12}$-alkyl, C$_1$-C$_{12}$-alkoxy, CF$_3$, OCF$_3$, CN, NO$_2$, COOM, COO-C$_1$-C$_{12}$-alkyl, SO$_3$M, CO-C$_1$-alkyl, CO-C$_6$-C$_{10}$-aryl, C$_5$-CO$_{10}$-aryl, hetaryl, and amino optionally substituted by C$_1$-C$_{12}$- alkyl, and
M denotes a proton, an alkali metal ion, an alkaline earth metal ion or an ammonium ion,
which comprises reacting, a compound of the formula (II)

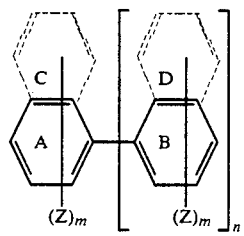

in which
Z represents N$_2$-, and
G represents sulphate or hydrogen sulphate,
with a compound of the formula (II)

R—CH=CH$_2$ in the presence of at least one organic or inorganic palladium salt as a catalyst and in at least one of water and an alcohol as solvent.

2. A process according to claim 1, in which the reaction is carried out in the presence of a base.

3. A process according to claim 1, in which an aryldiazonium salt is reacted with ethylene.

4. A process according to claim 1, in which as aryldiazonium salt a sulphoaryldiazonium salt is employed.

5. A process according to claim 1, in which the radical R in the formula (III) represents H or optionally substituted phenyl.

6. A process according to claim 1, in which as an aryldiazonium salt a sulphobenzenediazonium salt is employed.

7. A process according to claim 1, in which as an olefin, ethylene is passed into the reaction mixture with the aid of an intensive aeration device.

8. A process according to claim 7, in which the intensive aeration device for the ethylene is a surface aerator or a volume aerator, and the reaction mixture optionally being homogenised by an additional mixing element.

9. A process according to claim 1 wherein the starting material is a compound of the formula (IIa)

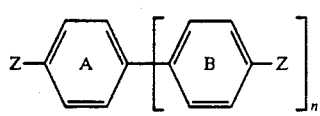 (IIa)
and the final product is a compound of the formula (Ia)
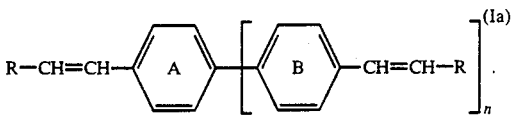
* * * * *

UNITED STATES PATENT AND TRADEMARK OFFICE
CERTIFICATE OF CORRECTION

PATENT NO. : 5,231,223

DATED : July 27, 1993

INVENTOR(S) : Bader et al.

It is certified that error appears in the above-identified patent and that said Letters Patent is hereby corrected as shown below:

| | |
|---|---|
| Title Page | ABSTRACT: Line 2 bottom of formula (I) after " CH=CH " insert -- - -- |
| Title Page | ABSTRACT: Line 7 delete " R-CH-CH$_2$ " and substitute -- R-CH=CH$_2$ -- |
| Col. 1, line 15 | Delete " 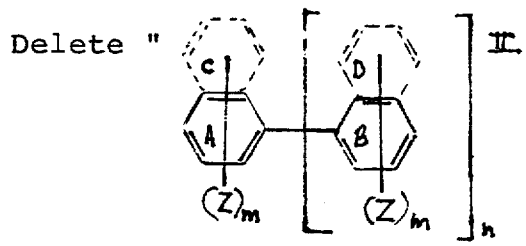 " and substitute |

-- 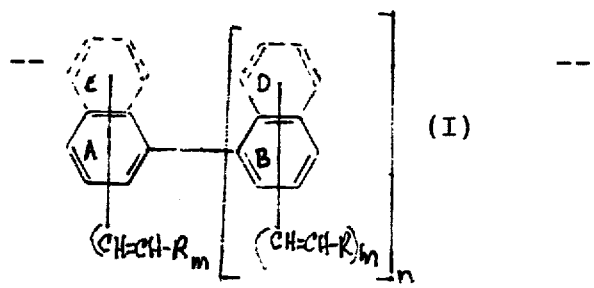 --  (I)

UNITED STATES PATENT AND TRADEMARK OFFICE
CERTIFICATE OF CORRECTION

PATENT NO. : 5,231,223
DATED : July 27, 1993
INVENTOR(S) : Bader et al.

It is certified that error appears in the above-identified patent and that said Letters Patent is hereby corrected as shown below:

Col. 1, line 48  Delete " 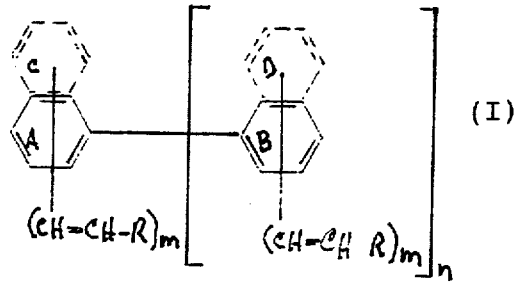 and substitute -- 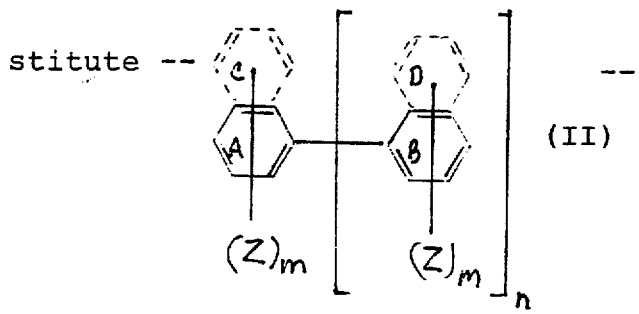 --

Col. 15, last line  After " CH=CH " insert -- - --

Col. 16, line 19  Delete " $C_5-CO_{10}$-aryl " and substitute -- $C_6-C_{10}$-aryl --

Col. 16, line 38  Delete " $N_2-$, " and substitute -- $N_2^{\oplus}G$ --

UNITED STATES PATENT AND TRADEMARK OFFICE
CERTIFICATE OF CORRECTION

PATENT NO. : 5,231,223

DATED : July 27, 1993

INVENTOR(S) : Bader et al.

It is certified that error appears in the above-identified patent and that said Letters Patent is hereby corrected as shown below:

Col. 16, line 41    Delete " (II) " and substitute -- (III) --

Signed and Sealed this

First Day of November, 1994

Attest:

BRUCE LEHMAN

Attesting Officer

Commissioner of Patents and Trademarks